(12) United States Patent
Lee et al.

(10) Patent No.: US 8,748,675 B2
(45) Date of Patent: Jun. 10, 2014

(54) EXTRACTIVE DISTILLATION OF CRUDE ALCOHOL PRODUCT

(75) Inventors: David Lee, Seabrook, TX (US); Lincoln Sarager, Houston, TX (US); Trinity Horton, Houston, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 200 days.

(21) Appl. No.: 13/162,034

(22) Filed: Jun. 16, 2011

(65) Prior Publication Data

US 2012/0323050 A1 Dec. 20, 2012

(51) Int. Cl.
*C07C 27/04* (2006.01)

(52) U.S. Cl.
USPC .............................. 568/885; 568/880; 568/881

(58) Field of Classification Search
None
See application file for complete search history.

(56) References Cited

U.S. PATENT DOCUMENTS

| | | | |
|---|---|---|---|
| 1,469,447 A | 10/1923 | Schneible | |
| 2,591,671 A | 4/1952 | Catterall et al. | |
| 2,591,672 A | 4/1952 | Catterall et al. | |
| 2,607,719 A | 8/1952 | Eliot et al. | |
| 2,649,407 A | 8/1953 | Harrison et al. | |
| 2,702,783 A | 2/1955 | Harrison et al. | |
| 2,715,604 A | 8/1955 | Weaver, Jr. | |
| 2,744,939 A | 5/1956 | Kennel | |
| 2,801,209 A | 7/1957 | Muller et al. | |
| 2,882,244 A | 4/1959 | Milton | |
| 2,901,404 A | 8/1959 | Kirshenbaum et al. | |
| 3,102,150 A | 8/1963 | Hunter et al. | |
| 3,130,007 A | 4/1964 | Breck | |
| 3,404,186 A | 10/1968 | Bailey et al. | |
| 3,408,267 A | 10/1968 | Miller et al. | |
| 3,445,345 A | 5/1969 | Katzen et al. | |
| 3,478,112 A | 11/1969 | Karl et al. | |
| 3,847,756 A | 11/1974 | Statman et al. | |
| 3,990,952 A | 11/1976 | Katzen et al. | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulprathipanja et al. | |
| 4,379,028 A * | 4/1983 | Berg et al. ...................... | 203/51 |
| 4,395,576 A | 7/1983 | Kwantes et al. | |
| 4,398,039 A | 8/1983 | Pesa et al. | |
| 4,421,939 A | 12/1983 | Kiff et al. | |
| 4,422,903 A | 12/1983 | Messick et al. | |
| 4,428,798 A | 1/1984 | Zudkevitch et al. | |
| 4,448,644 A | 5/1984 | Foster et al. | |
| 4,454,358 A | 6/1984 | Kummer et al. | |
| 4,455,198 A | 6/1984 | Zudkevitch et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,517,391 A | 5/1985 | Schuster et al. | |
| 4,520,213 A | 5/1985 | Victor | |
| 4,541,897 A | 9/1985 | Sommer et al. | |
| 4,559,109 A | 12/1985 | Lee et al. | |
| 4,569,726 A | 2/1986 | Berg et al. | |
| 4,600,571 A | 7/1986 | McCarroll et al. | |
| 4,626,321 A | 12/1986 | Grethlein et al. | |
| 4,631,115 A | 12/1986 | Berg et al. | |
| 4,654,123 A | 3/1987 | Berg et al. | |
| 4,678,543 A | 7/1987 | Houben et al. | |
| 4,692,218 A | 9/1987 | Houben et al. | |
| 4,761,505 A | 8/1988 | Diana et al. | |
| 4,774,365 A | 9/1988 | Chen et al. | |
| 4,777,303 A | 10/1988 | Kitson et al. | |
| 4,804,791 A | 2/1989 | Kitson et al. | |
| 4,842,693 A | 6/1989 | Wheldon | |
| 4,961,826 A | 10/1990 | Grethlein et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,026,908 A | 6/1991 | Smith et al. | |
| 5,035,776 A | 7/1991 | Knapp | |
| 5,061,671 A | 10/1991 | Kitson et al. | |
| 5,124,004 A | 6/1992 | Grethlein et al. | |
| 5,144,068 A | 9/1992 | Smith et al. | |
| 5,149,680 A | 9/1992 | Kitson et al. | |
| 5,185,481 A | 2/1993 | Muto et al. | |
| 5,215,902 A | 6/1993 | Tedder | |
| 5,227,141 A | 7/1993 | Kim et al. | |
| 5,233,099 A | 8/1993 | Tabata et al. | |
| 5,237,108 A | 8/1993 | Marraccini et al. | |
| 5,250,271 A | 10/1993 | Horizoe et al. | |
| 5,284,983 A | 2/1994 | Muto et al. | |
| 5,348,625 A | 9/1994 | Berg | |
| 5,415,741 A | 5/1995 | Berg | |
| 5,437,770 A | 8/1995 | Berg | |
| 5,445,716 A | 8/1995 | Berg | |

(Continued)

FOREIGN PATENT DOCUMENTS

| | | |
|---|---|---|
| CN | 201768393 | 3/2011 |
| CN | 102091429 | 6/2011 |

(Continued)

OTHER PUBLICATIONS

International Search Report and Written Opinion mailed Jun. 13, 2012 in corresponding International Application No. PCT/US2011/059894.

(Continued)

*Primary Examiner* — Sudhakar Katakam

(57) ABSTRACT

Recovery of ethanol from a crude ethanol product obtained from the hydrogenation of acetic acid using an extractive distillation column. The column yields a residue that comprises ethanol, acetic acid, and the extractive agent. The extractive agent may be water and may be separated from the residue and returned to the extractive distillation column.

21 Claims, 3 Drawing Sheets

(56) References Cited

U.S. PATENT DOCUMENTS

| | | |
|---|---|---|
| 5,449,440 A | 9/1995 | Rescalli et al. |
| 5,488,185 A | 1/1996 | Ramachandran et al. |
| 5,565,068 A | 10/1996 | Parker et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Gaddy et al. |
| 5,993,610 A | 11/1999 | Berg |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,375,807 B1 | 4/2002 | Nieuwoudt et al. |
| 6,462,231 B1 | 10/2002 | Yanagawa et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,809,217 B1 * | 10/2004 | Colley et al. ............. 560/231 |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,351,559 B2 | 4/2008 | Verser et al. |
| 7,361,794 B2 | 4/2008 | Grosso |
| 7,399,892 B2 | 7/2008 | Rix et al. |
| 7,507,562 B2 | 3/2009 | Verser et al. |
| 7,553,397 B2 | 6/2009 | Colley et al. |
| 7,572,353 B1 | 8/2009 | Vander et al. |
| 7,594,981 B2 | 9/2009 | Ikeda |
| 7,601,865 B2 | 10/2009 | Verser et al. |
| 7,608,744 B1 | 10/2009 | Johnston et al. |
| 7,682,812 B2 | 3/2010 | Verser et al. |
| 7,732,173 B2 | 6/2010 | Mairal et al. |
| 7,744,727 B2 | 6/2010 | Blum et al. |
| 7,790,938 B2 | 9/2010 | Kawasaki et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 8,053,610 B2 | 11/2011 | Kikuchi et al. |
| 8,062,482 B2 | 11/2011 | Warner |
| 8,128,826 B2 | 3/2012 | Plante et al. |
| 8,129,436 B2 | 3/2012 | Tirtowidjojo et al. |
| 8,198,057 B2 | 6/2012 | Padgett |
| 8,288,596 B2 | 10/2012 | Garton et al. |
| 8,299,132 B2 | 10/2012 | Gracey et al. |
| 8,299,133 B2 | 10/2012 | Gracey et al. |
| 2005/0197506 A1 | 9/2005 | Scates et al. |
| 2006/0019360 A1 | 1/2006 | Verser et al. |
| 2006/0127999 A1 | 6/2006 | Verser et al. |
| 2007/0138083 A1 | 6/2007 | Aizawa |
| 2007/0144886 A1 | 6/2007 | Sylvester et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0281354 A1 | 11/2009 | Mariansky et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |
| 2011/0082322 A1 | 4/2011 | Jevtic et al. |
| 2012/0273338 A1 | 11/2012 | Lee |
| 2012/0323049 A1 | 12/2012 | Lee |

FOREIGN PATENT DOCUMENTS

| | | |
|---|---|---|
| CN | 101525272 | 5/2012 |
| DE | 2723611 | 11/1978 |
| EP | 0104197 | 4/1984 |
| EP | 0137749 | 4/1985 |
| EP | 0167300 | 1/1986 |
| EP | 0234508 | 9/1987 |
| EP | 0456647 | 11/1991 |
| EP | 2060553 | 5/2009 |
| EP | 2060553 A1 * | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4193304 A | 7/1992 |
| JP | 2009-263356 | 11/2009 |
| JP | 2010-159212 | 7/2010 |
| WO | WO 83/03409 | 10/1983 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2010/055285 | 5/2010 |
| WO | WO 2011/097220 A2 | 8/2011 |
| WO | WO 2011/097227 | 8/2011 |
| WO | WO 2012/006219 | 1/2012 |

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al.,(2005). Experimental and DFT studies of the conversion of ethanol and acetic acid on PtSn-based catalysts, Journal of Physical Chemistry, 109(6), 2074-2085.

Hilmen, "Separation of Azeotropic Mixtures: Tools for Analysis and Studies on Batch Distillation Operation" (Nov. 2000) p. 17-20.

Xu, et al., "Kinetics of Acetic Acid Esterification over Ion Exchange Catalysts", Canadian Journal of Chemical Engineering, vol. 74, Aug. 1, 1996, XP 009084826, pp. 493-500.

V. Ragaini et al., "Increasing the value of dilute acetic acid streams through esterification Part 1. Experimental analysis of the reaction zone", Applied Catalysis B: Environmental, vol. 64, 2006, pp. 66-71.

(56) References Cited

OTHER PUBLICATIONS

Anonymous: "Studies in Extractive and Azeotropic Distillation Series; Study No. 4—Separation of Alcohols from the Acetate/Alcohol/Water Ternary by Extractive Distillation" May 9, 2008, pp. 1-9.

Kita H., et al., "Synthesis of a Zeolite NAA Membrane for Pervaporation of Water/Organic Liquid Mixtures", Journal of Materials Science Letters, vol. 14, Jan. 1, 1995, pp. 206-208.

Calvar, et al., "Esterification of acetic acid and ethanol: Reaction kinetics and operation in a packed bed reactive distillation column", Chem Engineering and Processing, vol. 46, No. 12, Oct. 9, 2007, pp. 1317-1323.

Marian Simo, et al., "Adsorption/Desorption of Water and Ethanol on 3A Zeolite in Neo-Adiabatic Fixed Bed", Industrial and Engineering Chemistry Research, vol. 48, No. 20, Sep. 25, 2009, pp. 9247-9260.

Kaj Jakobsson et al., "Modeling of a side reactor configuration combining reaction and distillation", Chemical Engineering Science, vol. 57, 2002, pp. 1521-1524.

Benson, Tracy J., et al., "Cellulose Based Adsorbent Materials for the Dehydration of Ethanol Using Thermal Swing Adsorption", Adsorption, Kluwer Academic Publishers, vol. 11, No. 1, Jul. 1, 2005, pp. 697-701.

H. Constantin et al., "Influence of C-Sources on the Denitrification Rate of a High-Nitrate Concentrated Industrial Wastewater", Wat. Res. vol. 31, No. 3, 1997, pp. 583-589.

Y. Zhu et al., "Techno-economic Analysis for the Thermochemical Conversion of Lignocellulosic Biomass to Ethanol via Acetic Acid Synthesis", Apr. 1, 2009, pp. 1-71 (80 Pages).

International Search Report and Written Opinion for PCT/US2012/035175 mailed Nov. 15, 2012.

Response to Final Office Action for U.S. Appl. No. 13/162,005 filed Nov. 26, 2013.

* cited by examiner

EXTRACTIVE DISTILLATION OF CRUDE ALCOHOL PRODUCT

FIELD OF THE INVENTION

The present invention relates generally to processes for producing ethanol from acetic acid in a hydrogenation reactor and, in particular, to an extractive distillation process for recovering ethanol.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP2060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

Others have proposed various extractive agents for separating mixtures of ethanol, ethyl acetate and water. U.S. Pat. No. 4,654,123 describes a process for separating ethanol from water using extractive agents. U.S. Pat. Nos. 4,379,028 and 4,569,726 describe processes for recovering ethyl acetate from an ethyl acetate/ethanol/water mixture using extractive agents. U.S. Pat. No. 6,375,807 describes a method of separating ethanol and ethyl acetate using extractive agents.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol comprising the steps of hydrogenating acetic acid from an acetic acid feed stream in a reactor to form a crude ethanol product comprising ethanol, ethyl acetate, and acetic acid; separating at least a portion of the crude ethanol product in a first column in the presence of one or more extractive agents into a first distillate comprising ethyl acetate, and a first residue comprising ethanol, acetic acid, and the one or more extractive agents; and recovering ethanol from the first residue. The extractive agent may also be recovered from the first residue and returned to the first column.

The one or more extractive agents are selected from a group consisting of water, dimethylsulfoxide, glycerine, diethylene glycol, 1-naphthol, hydroquinone, N,N'-dimethylformamide, 1,4-butanediol, ethylene glycol-1,5-pentanediol, propylene glycol-tetraethylene glycol-polyethylene glycol, glycerine-propylene glycol-tetraethylene glycol-1,4-butanediol, ethyl ether, methyl formate, cyclohexane, N,N' dimethyl-1,3-propanediamine, N,N'-dimethylethylenediamine, diethylene triamine, hexamethylene diamine, 1,3-diaminopentane, and alkylated thiopene, dodecane, tridecane, tetradecane, chlorinated paraffins, and mixtures thereof.

In a second embodiment, the present invention is directed to a process for producing ethanol comprising the steps of providing a crude ethanol product comprising ethanol, acetic acid, and ethyl acetate; separating at least a portion of the crude ethanol product in a first column in the presence of one or more extractive agents into a first distillate comprising ethyl acetate, and a first residue comprising ethanol, acetic acid, and the one or more extractive agents; and recovering ethanol from the first residue.

In a third embodiment, the present invention is directed to a process for producing ethanol comprising the steps of hydrogenating acetic acid from an acetic acid feed stream in a reactor to form a crude ethanol product comprising ethanol, ethyl acetate, water, and acetic acid; feeding an extractive agent comprising water and at least a portion of the crude ethanol product to a first column; separating at least a portion of the crude ethanol product in a first column into a first distillate comprising ethyl acetate, and a first residue comprising ethanol, acetic acid, and water; and recovering the extractive agent from the first residue.

In a fourth embodiment, the present invention is directed to a process for producing ethanol, comprising hydrogenating acetic acid from an acetic acid feed stream in a reactor to form a crude ethanol product comprising ethanol, and ethyl acetate, separating at least a portion of the crude ethanol product in a first column in the presence of one or more extractive agents into a first distillate comprising ethyl acetate, and a first residue comprising ethanol, and the one or more extractive agents, and recovering ethanol from the first residue.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

Figure 1:
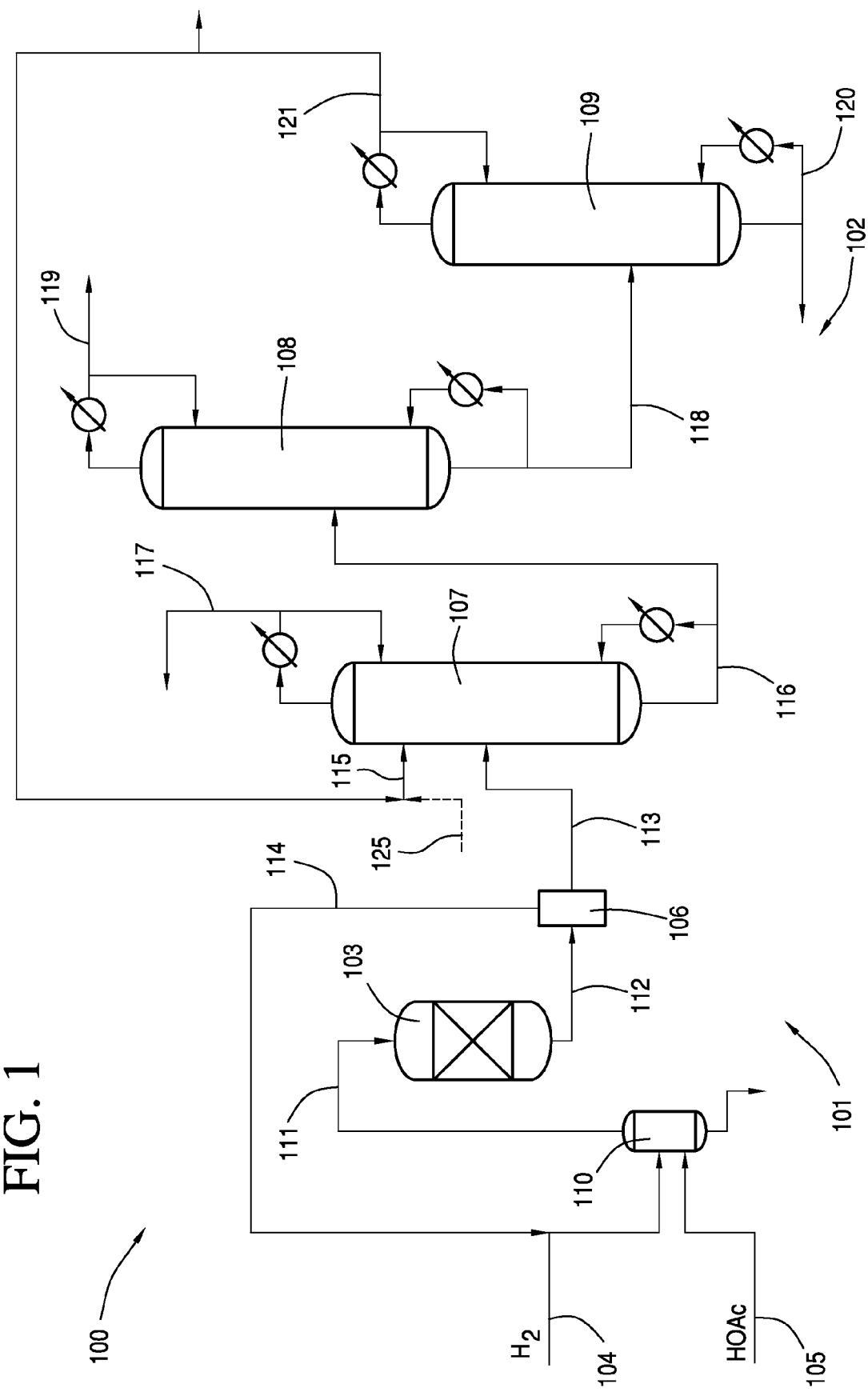
FIG. 1 is a schematic diagram of an ethanol production system with distillation columns to recover the extractive agent, water, from acetic acid in accordance with one embodiment of the present invention.

The present invention relates to processes for recovering ethanol produced by hydrogenating acetic acid in the presence of a catalyst. The hydrogenation reaction produces a crude ethanol product that comprises ethanol, water, ethyl acetate, unreacted acetic acid, and other impurities. Ethyl acetate is difficult to separate from a mixture of ethyl acetate and ethanol by distillation because of the closeness in boiling points between ethyl acetate and ethanol. The presence of other components in the crude ethanol product such as ethyl acetate, acetic acid and acetaldehyde, depending on concentration, may further complicate the separation of ethanol and ethyl acetate.

To improve efficiencies in recovering ethanol from the crude ethanol product, the processes of the present invention involve recovering ethanol from the crude ethanol product using one or more extractive agents in an initial (first) separation column. Ethanol, water, and acetic acid are withdrawn as the residue. Ethyl acetate and other light organics are withdrawn as the distillate. Specifically, the present invention provides processes for separating ethyl acetate and ethanol from the crude ethanol product in an initial separation column using one or more extractive agents. By using one or more extractive agents, an ethanol product may be recovered having a reduced ethyl acetate content. In addition, the use of one or more extractive agents may beneficially reduce the energy required to recover ethanol with low amounts of ethyl acetate.

The presence of the extractive agents allows the ethanol product to be separated from the ethyl acetate by-product more effectively. Using an extractive agent in accordance with embodiments of the present invention allows for a majority of the ethyl acetate to be recovered from the crude ethanol product. Preferably, at least 90% of the ethyl acetate in the crude ethanol product is recovered through the first distillate, e.g., at least 95% of the ethyl acetate or at least 98% of the ethyl acetate. Recovering a majority of the ethyl acetate provides for low concentrations of ethyl acetate in the residue from the initial column, e.g., less than 1 wt. %, less than 0.3 wt. % or less than 0.01 wt. %. Thus, it is not necessary to engage in additional separations of ethanol and ethyl acetate when recovering ethanol from the residue.

Advantageously, this separation approach results in reducing energy requirements to recover ethanol from the crude ethanol product.

The extractive agent preferably has a boiling point higher than major components in the distillate. In preferred embodiments, the extractive agent employed has a boiling point greater than 80° C., e.g., greater than 85° C., or greater than 100° C. Extractive agents having boiling points greater than 200° C. are also contemplated. A preferred extractive agent comprises water. The water may be produced in the hydrogenation reactor and recycled as the extractive agent. Other suitable extractive agents include, for example, dimethylsulfoxide, glycerine, diethylene glycol, 1-naphthol, hydroquinone, N,N'-dimethylformamide, 1,4-butanediol, ethylene glycol-1,5-pentanediol, propylene glycol-tetraethylene glycol-polyethylene glycol, glycerine-propylene glycol-tetraethylene glycol-1,4-butanediol, ethyl ether, methyl formate, cyclohexane, N,N' dimethyl-1,3-propanediamine, N,N'-dimethylethylenediamine, diethylene triamine, hexamethylene diamine, 1,3-diaminopentane, and alkylated thiopene, dodecane, tridecane, tetradecane and chlorinated paraffins. These other agents may be used with water. Some suitable extraction agents include those described in U.S. Pat. Nos. 4,379,028; 4,569,726; 5,993,610; and 6,375,807, the entireties of which are incorporated herein by reference.

In one embodiment, the extractive agents may be fed to the initial column for processing the crude ethanol product. In another embodiment, the extractive agents are fed to and combined with the crude ethanol product prior to being introduced into the initial column. Preferably, a substantial portion of the ethanol, water, and acetic acid is removed from the crude ethanol product as the residue from the initial column. The residue stream, for example, may comprise from 30 to 90% of the water and from 85% to 100% of the acetic acid from the crude ethanol product. The residue stream may also comprise the extractive agent, water, and thus the water concentration in the residue may exceed the water concentration of the crude ethanol product. The extractive agents may be recovered from the residue, e.g., in one or more additional separation columns, and recycled to the initial column.

Generally, the distillate from the initial column may comprise ethyl acetate and acetaldehyde. The distillate may be recycled in whole or part to the hydrogenation reactor. In some embodiments, the distillate from the initial column may also comprise ethanol and preferably less than 15 wt. % water, less than 7.5 wt. % water, less 4 wt. % water or less than 2 wt. % water. In one embodiment, a light ends column may be used to further separate the distillate into ethyl acetate stream, which is recycled to the hydrogenation reactor, and ethanol stream.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a by-product of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain NorPro. The Saint-Gobain NorPro SS61138 silica exhibits the following properties: contains approximately 95 wt. % high surface area silica; surface area of about 250 $m^2$/g; median pore diameter of about 12 nm; average pore volume of about 1.0 $cm^3$/g as measured by mercury intrusion porosimetry and a packing density of about 0.352 g/$cm^3$ (22 lb/$ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary components ranges of the crude ethanol are provided in Table 1. The other components identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

In one embodiment, the weight ratio of ethanol to water may be at least 0.18:1 or greater, e.g., at least 0.5:1 or at least 1:1. In terms of ranges the weight ratio of ethanol to water may be from 0.18:1 to 5:1, e.g., from 0.5:1 to 3:1 or from 1:1 to 2:1. Preferably the crude ethanol product has more ethanol than water compared to conventional fermentation processes of ethanol. In one embodiment, the lower amounts of water may require less energy to separate the ethanol and improves the overall efficiency of the process. Thus, in preferred embodiments, the amount of ethanol in the crude ethanol product is from 15 wt. % to 70 wt. %, e.g., from 20 wt. % to 70 wt. % or from 25 wt. % to 70 wt. %. Higher ethanol weight percents are particularly preferred.

Ethanol Recovery

Figure 2:
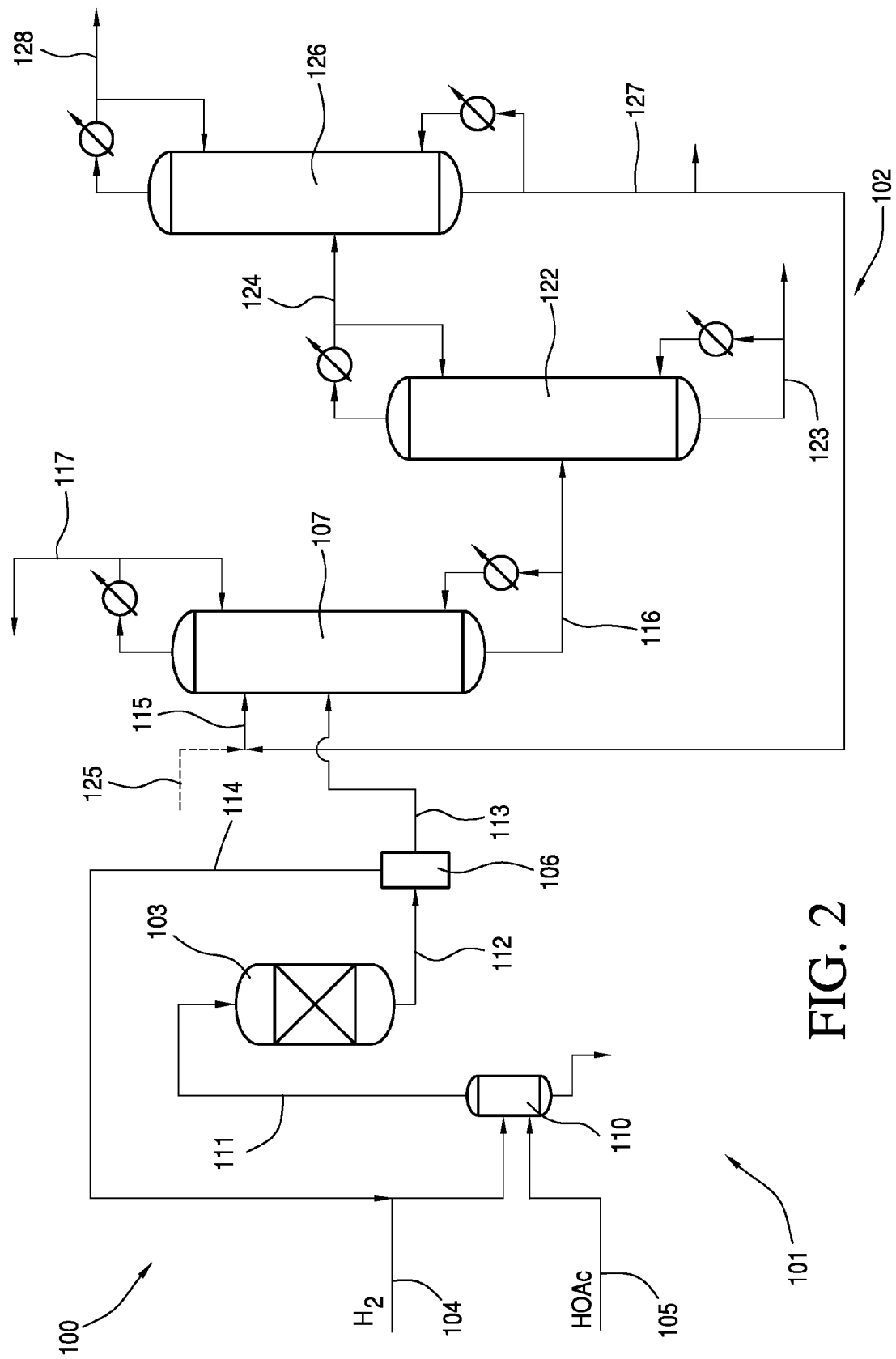
FIG. 2 is a schematic diagram of an ethanol production system with distillation columns to recover the extractive agent, water, from ethanol in accordance with one embodiment of the present invention.
Figure 3:
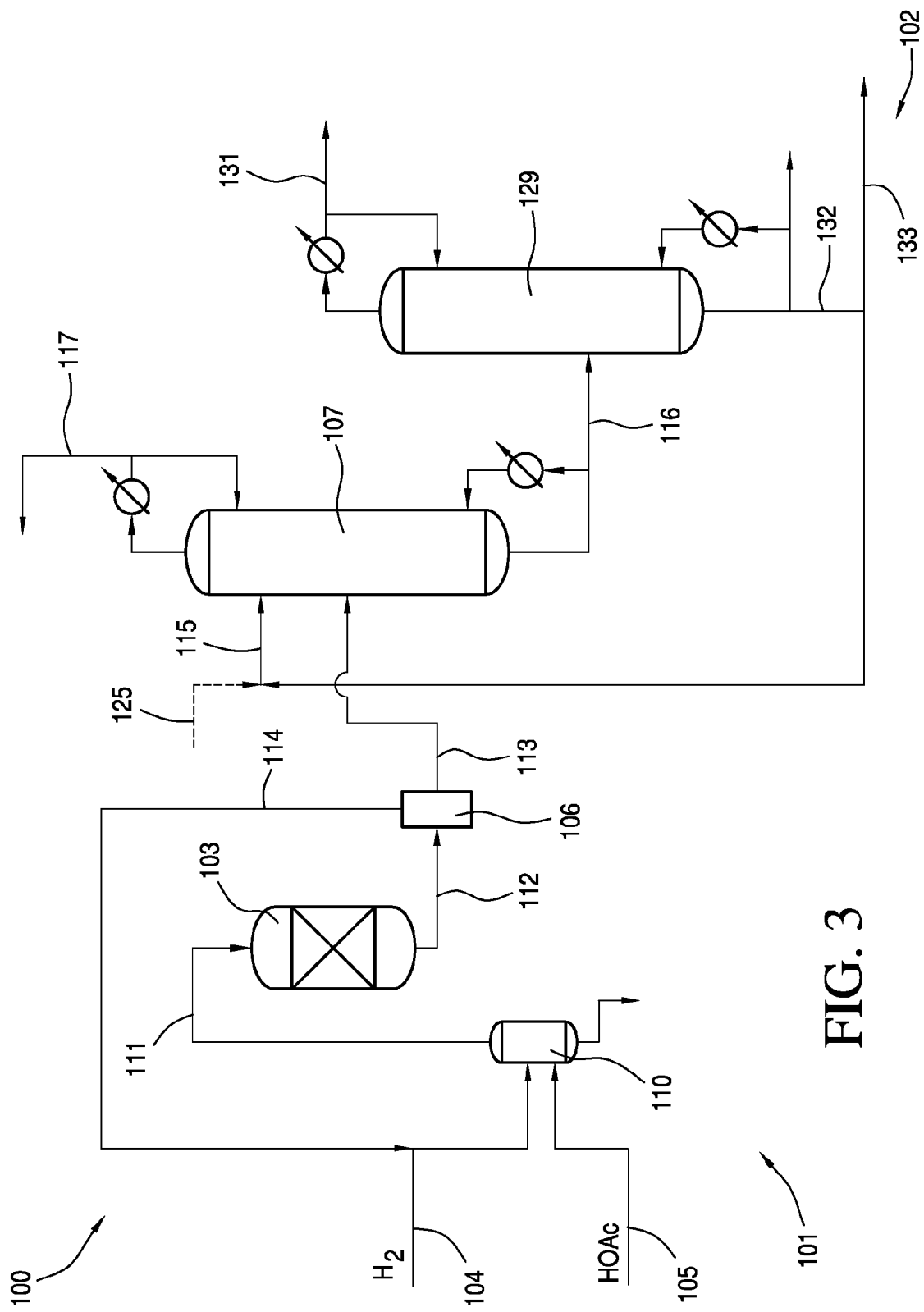
FIG. 3 is a schematic diagram of an ethanol production system with distillation columns to recover the extractive agent, water, in accordance with one embodiment of the present invention.

Exemplary ethanol recovery systems in accordance with embodiments of the present inventions are shown in FIGS. 1-3. Each hydrogenation system 100 includes a suitable hydrogenation reactor and a process for separating ethanol from the resulting crude ethanol mixture. System 100 comprises reaction zone 101 and separation zone 102. For purposes of describing system 100 the extractive agent used in FIGS. 1-3 is water. In separation zone 102 for FIG. 1, the extractive agent is separated from acetic acid. FIG. 2, the extractive agent is separated from ethanol after removing acetic acid. In FIG. 3, the extractive agent is separated from ethanol without separately removing acetic acid. System 100 shown in FIG. 3 may be suitable for high acetic acid conversion where the content of acetic acid is low.

Reaction zone 101 comprises reactor 103, hydrogen feed line 104 and acetic acid feed line 105. Hydrogen and acetic acid are fed to a vaporizer 110 via lines 104 and 105, respectively, to create a vapor feed stream in line III that is directed to reactor 103. In one embodiment, lines 104 and 105 may be combined and jointly fed to the vaporizer 110, e.g., in one stream containing both hydrogen and acetic acid. The temperature of the vapor feed stream in line III is preferably from 100° C. to 350° C., e.g., from 120° C. to 310° C. or from 150° C. to 300° C. Any feed that is not vaporized is removed from vaporizer 110, as shown in FIG. 1, and may be recycled or discarded. In addition, although FIG. 1 shows line 111 being directed to the top of reactor 103, line 111 may be directed to the side, upper portion, or bottom of reactor 103. Further modifications and additional components to reaction zone 101 and separation zone 102 are described below.

Reactor 103 contains the catalyst that is used in the hydrogenation of the carboxylic acid, preferably acetic acid, to ethanol. In one embodiment, one or more guard beds (not shown) may be used upstream of the reactor, optionally upstream of vaporizer 110, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 112.

The crude ethanol product stream in line 112 may be condensed and fed to a separator 106, which, in turn, provides a vapor stream 114 and a liquid stream 113. The separator 106, for example, may comprise one or more flashers or knockout pots. The separator 106 may operate at a temperature of from 20° C. to 250° C., e.g., from 30° C. to 225° C. or from 60° C. to 200° C. The pressure of separator 106 may be from 50 kPa to 2000 kPa, e.g., from 75 kPa to 1500 kPa or from 100 kPa to 1000 kPa. Optionally, the crude ethanol product in line 112 may pass through one or more membranes to separate hydrogen and/or other non-condensable gases.

The vapor stream 114 exiting separator 106 may comprise hydrogen and hydrocarbons, and may be purged and/or returned to reaction zone 101. As shown, vapor stream 114 is combined with the hydrogen feed 104 and co-fed to vaporizer 110. In some embodiments, the returned vapor stream 114 may be compressed before being combined with hydrogen feed 104.

The liquid stream 113 from separator 106 is withdrawn and pumped to first column 107, also referred to as an "extractive column."

In one embodiment, the contents of liquid stream 113 are substantially similar to the crude ethanol product obtained from the reactor, except that the composition has been depleted of hydrogen, carbon dioxide, methane and/or ethane, which are preferably removed by separator 106. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

LIQUID STREAM 113

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 0.01 to 80 | 1 to 70 |
| Water | 5 to 40 | 5 to 30 | 10 to 30 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof.

The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 113, may comprise propanol, e.g., isopropanol and/or n-propanol, in an amount from 0.001 to 0.1 wt. %, from 0.001 to 0.05 wt. % or from 0.001 to 0.03 wt. %. It should be understood that these other components may be carried through in any of the distillate or residue streams described herein and will not be further described herein, unless indicated otherwise.

Optionally, crude ethanol product in line 112 or in liquid stream 113 may be further fed to an esterification reactor, hydrogenolysis reactor, or combination thereof. An esterification reactor may be used to consume acetic acid present in the crude ethanol product to further reduce the amount of acetic acid to be removed. Hydrogenolysis may be used to convert ethyl acetate in the crude ethanol product to ethanol.

Liquid stream 113 is introduced in the upper part of first column 107, e.g., upper half or upper third. As shown, one or more extractive agents, as described above, are also introduced to column 107 via line 115 to aid with the separation of ethanol from water (and other components). Preferably, the extractive agent is recovered directly or indirectly from the first residue and recycled back to first column 107, as shown in FIGS. 1 and 2, optionally with the addition of fresh extractive agent as indicated by 125. The extractive agent is preferably introduced near the top of the column and flows downward until it reaches the reboiler. The extractive agent in line 115 ideally is introduced above the feed point of the liquid stream 113.

The amount of extractive agent fed to extractive column 107 may vary widely. For example, when the extractive agent in line 115 comprises water, the mass flow ratio of water to crude ethanol product may range from 2:1 to 1:15, e.g., from 1:1.1 to 1:12 or from 1:1.2 to 1:10.

The crude ethanol product in liquid stream 113 comprises ethyl acetate, ethanol and water. These compounds may form various binary and tertiary azeotropes. For example, a tertiary azeotrope may have a boiling point lower than its constituents, while other tertiary azeotropes may have a boiling point in between the pure constituents. In the embodiments of the present invention, without the use of an extractive agent, a larger portion of the ethyl acetate would leak into the first residue in line 116. By using an extractive agent in column 107, the separation of ethanol into the first residue in line 116, with minimal amounts of ethyl acetate, is facilitated thus increasing the yield of the overall ethanol product in the first residue in line 116.

In this manner, ethanol water, unreacted acetic acid, and other heavy components, if present, are removed from the liquid stream 113 and are withdrawn, preferably continuously, as first residue in line 116. First column 107 also forms a first distillate, which is withdrawn in line 117, and which may be condensed and refluxed, for example, at a ratio of from 30:1 to 1:30, e.g., from 10:1 to 1:10 or from 5:1 to 1:5.

When column 107 is operated under about 170 kPa, the temperature of the residue exiting in line 116 preferably is from 70° C. to 155° C., e.g., from 90° C. to 130° C. or from 100° C. to 110° C. The temperature of the distillate exiting in line 117 preferably is from 30° C. to 100° C., e.g., from 60° C. to 85° C. or from 65° C. to 80° C. In some embodiments, the pressure of first column 107 may range from 0.1 kPa to 510 kPa, e.g., from 1 kPa to 475 kPa or from 1 kPa to 375 kPa. Exemplary compositions of the first distillate and the first residue for first column 107 are provided in Table 3 below. It should also be understood that the distillate and residue may also contain other components, not listed in Table 3. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

EXTRACTIVE COLUMN 107

|  | Conc. (wt. %) | Conc. (wt. %) | Conc. (wt. %) |
|---|---|---|---|
| First Distillate |  |  |  |
| Ethanol | <20 | 0.1 to 15 | 0.5 to 10 |
| Water | 1 to 30 | 2 to 25 | 4 to 15 |
| Acetic Acid | <0.2 | <0.01 | not detectable |
| Ethyl Acetate | 35 to 95 | 35 to 80 | 35 to 60 |
| Acetaldehyde | <35 | 0.1 to 30 | 5 to 30 |
| Acetal | <35 | 0.1 to 30 | 5 to 30 |
| First Residue |  |  |  |
| Acetic Acid | 0.1 to 50 | 0.5 to 40 | 1 to 30 |
| Water | 40 to 85 | 50 to 80 | 55 to 75 |
| Ethanol | 10 to 80 | 15 to 60 | 15 to 45 |
| Ethyl Acetate | <1.0 | <0.3 | <0.01 |

Water in the residue includes both the water produced in the hydrogenation reactor that is present in the crude ethanol product and water fed to column 107 as the extractive agent 115. As more water is fed as the extractive agent, the amount of water in the residue will increase. The increase in amount of extractive agent fed may also further decrease the leakage of ethyl acetate in the first residue. For example, the ethyl acetate concentration in the first residue may be very low and may range from 1 wppm to 800 wppm and more preferably from 5 wppm to 250 wppm.

In an embodiment of the present invention, column 107 utilizes an extractive agent to aid in the separation of ethyl acetate and ethanol. Thus, most of the ethanol, water, and acetic acid are removed from the residue stream and only a small amount of ethanol and water is collected in the distillate stream. The weight ratio of ethanol in the residue in line 116 to ethanol in the distillate in line 117 may be greater than 1:1, e.g., greater than 2:1. The weight ratio of water in the residue to the water in the distillate may be greater than 1:1, e.g., greater than 2:1.

Some species, such as acetals, may decompose in first column 107 such that very low amounts, or even no detectable amounts, of acetals remain in the distillate or residue. In addition, an equilibrium reaction between acetic acid and ethanol or between ethyl acetate and water may occur in the crude ethanol product after it exits the reactor 103. Depending on the concentration of acetic acid in the crude ethanol product, this equilibrium may be driven toward formation of ethyl acetate. This equilibrium may be regulated using the residence time and/or temperature of crude ethanol product.

As shown in FIG. 1, the residue stream 116 is introduced to a second column 108, also referred to as an "acid separation column," because acid, if any, from the first residue 116 is removed in second column 108. An acid separation column may be used when the acetic acid concentration in the first residue is greater than 1 wt. %, e.g., greater than 5 wt. %. In some embodiments, when the acetic acid concentration is low, e.g., less than 10 wt. %, the water separation column in FIG. 3 may be used.

In FIG. 1, the first residue in line 116 is introduced to second column 108, preferably in the middle part of column 108, e.g., middle half or middle third. Second column 108 yields a second residue in line 118 comprising acetic acid and water, and a second distillate in line 119 comprising ethanol. Second column 108 may be a tray column or packed column. In one embodiment, second column 108 is a tray column having from 5 to 150 trays, e.g., from 15 to 50 trays or from 20 to 45 trays. Although the temperature and pressure of second column 108 may vary, when at atmospheric pressure the temperature of the second residue exiting in line 118 from second column 108 preferably is from 95° C. to 130° C., e.g., from 100° C. to 125° C. or from 110° C. to 120° C. The temperature of the second distillate exiting in line 119 from second column 108 preferably is from 60° C. to 105° C., e.g., from 75° C. to 100° C. or from 80° C. to 100° C. The pressure of second column 108 may range from 0.1 kPa to 510 kPa, e.g., from 1 kPa to 475 kPa or from 1 kPa to 375 kPa. Exemplary components for the distillate and residue compositions for second column 108 are provided in Table 4 below. It should be understood that the distillate and residue may also contain other components, not listed in Table 4.

TABLE 4

ACID SEPARATION COLUMN 108 (FIG. 1)

| | Conc. (wt. %) | Conc. (wt. %) | Conc. (wt. %) |
|---|---|---|---|
| Second Distillate | | | |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 1 to 25 | 5 to 20 |
| Second Residue | | | |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 119 to ethanol in the second residue in line 118 preferably is at least 35:1. In one embodiment, the weight ratio of water in the second residue 118 to water in the second distillate 119 is greater than 2:1, e.g., greater than 4:1 or greater than 6:1. In addition, the weight ratio of acetic acid in the second residue 118 to acetic acid in the second distillate 119 preferably is greater than 10:1, e.g., greater than 15:1 or greater than 20:1. Preferably, the second distillate in line 119 is substantially free of acetic acid and may only contain, if any, trace amounts of acetic acid. A reduced concentration of acetic acid in line 119 advantageously provides an ethanol product that also has no amount or a trace amount of acetic acid. Preferably, the second distillate in line 119 contains substantially no ethyl acetate. The second distillate in line 119 may be withdrawn as the ethanol product or further processed to reduce water concentration.

In FIG. 1, to recover the water as the extractive agent for use in first column 107, the second residue in line 118 is further separated into a water stream and an acetic acid stream. As shown in FIG. 1 there is provided a distillation column, however, other separation units, such as a membrane, may be used to separate second residue in line 118. The second residue in line 118 is introduced to a third column 109, preferably in the top part of column 109, e.g., top half or top third. The third distillate in line 121 preferably comprises water and very low amount of acetic acid, e.g., less than 1 wt. %, or less than 0.5 wt. %. The third distillate in line 121 may be returned to first column 107 as extractive agent in line 115 or may be purged as necessary.

Third column 109 may be a tray column or packed column. In one embodiment, third column 109 is a tray column having from 5 to 150 trays, e.g., from 15 to 50 trays or from 20 to 45 trays. Although the temperature and pressure of third column 109 may vary, when at atmospheric pressure the temperature of the third residue exiting in line 120 preferably is from 115° C. to 140° C., e.g., from 120° C. to 135° C. or from 125° C. to 135° C. The temperature of the third distillate exiting in line 121 at atmospheric pressure preferably is from 90° C. to 110° C., e.g., from 95° C. to 110° C. or from 100° C. to 110° C. The pressure of third column 109 may range from 0.1 kPa to 510 kPa, e.g., from 1 kPa to 475 kPa or from 1 kPa to 375 kPa.

In other embodiments of the present invention, acetic acid and water may be separated using membranes, adsorption, reactive distillation column, azeotropic distillation, and others as described herein. Depending on the amount of water and acetic acid contained in the third residue of third column 109, third residue in line 120 may be treated in one or more of the following processes. The following are exemplary processes for further treating third residue and it should be understood that any of the following may be used regardless of acetic acid concentration. When the residue comprises a majority of acetic acid, e.g., greater than 70 wt. %, the residue may be recycled to the reactor without any separation of water. In one embodiment, the residue may be separated into an acetic acid stream and a water stream when the residue comprises a majority of acetic acid, e.g., greater than 50 wt. %. Acetic acid may also be recovered in some embodiments from third residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where third residue in line 120 comprises less than 50 wt. % acetic acid, possible options include one or more of: (i) returning a portion of the third residue to reactor 103, (ii) neutralizing the acetic acid, (iii) reacting the acetic acid with an alcohol, or (iv) disposing of the third residue in a waste water treatment facility. It also may be possible to separate second and/or third residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the third residue in line 120 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the third residue comprises very minor amounts of acetic acid, e.g., less than 5 wt. %, the third residue may be disposed of to a waste water treatment facility without further processing. The organic content, e.g., acetic acid content, of the second distillate beneficially may be suitable to feed microorganisms used in a waste water treatment facility.

The acid separation column may also be operated in a manner that withdraws a second residue that comprises acetic acid and a second distillate that comprises ethanol and water. In FIG. 2, second column 122 may be a tray column or packed column. In one embodiment, second column 122 is a tray column having from 5 to 70 trays, e.g., from 15 to 50 trays or from 20 to 45 trays. When column 122 is operated under standard atmospheric pressure, the temperature of the residue exiting in line 123 preferably is from 95° C. to 130° C., e.g., from 105° C. to 117° C. or from 110° C. to 115° C. The temperature of the distillate exiting in line 124 from column 107 preferably is from 70° C. to 110° C., e.g., from 75° C. to 95° C. or from 80° C. to 90° C. In other embodiments, the pressure of first column 107 may range from 0.1 KPa to 510 KPa, e.g., from 1 KPa to 475 KPa or from 1 KPa to 375 KPa. Exemplary components for the distillate and residue compositions for second column 122 are provided in Table 5 below.

TABLE 5

ACID SEPARATION COLUMN 122 (FIG. 2)

|  | Conc. (wt. %) | Conc. (wt. %) | Conc. (wt. %) |
|---|---|---|---|
| Distillate |  |  |  |
| Ethanol | 10 to 85 | 15 to 45 | 20 to 40 |
| Water | 10 to 90 | 50 to 80 | 60 to 80 |
| Acetic Acid | <2 | 0.001 to 0.5 | 0.01 to 0.2 |
| Ethyl Acetate | <0.5 | <0.01 | 0.001 to 0.01 |
| Acetaldehyde | <2 | <0.01 | 0.001 to 0.01 |
| Residue |  |  |  |
| Acetic Acid | 60 to 100 | 65 to 100 | 85 to 95 |
| Water | <30 | 0.5 to 30 | 1 to 15 |
| Ethanol | <1 | <0.9 | <0.07 |

The second residue in line 123 may be recycled to reaction zone 101 or treated as discussed above to remove water.

As shown in FIG. 2, the remaining water, if any, from the second distillate in line 124 may be removed in further embodiments of the present invention. Depending on the water concentration, the ethanol product may be derived from the second distillate in line 124. Some applications, such as industrial ethanol applications, may tolerate water in the ethanol product, while other applications, such as fuel applications, may require an anhydrous ethanol. Water may be removed from the second distillate in line 124 using several different separation techniques. Particularly preferred techniques include the use of distillation column, membranes, adsorption units and combinations thereof.

As shown, the second distillate in line 124 is fed to a third column 126, e.g., ethanol product column, for separating the distillate into a third distillate (ethanol distillate) in line 128 and a third residue (water residue) in line 127. The third residue in line 127 or a portion thereof may be returned to first column 107 as an extractive agent. Depending on the amount of water needed as the extractive agent a portion of third residue in line 127 may also be purged. Second distillate in line 124 may be introduced into the lower part of column 126, e.g., lower half or lower third. Third distillate 128 preferably is refluxed, for example, at a reflux ratio of from 1:10 to 10:1, e.g., from 1:3 to 3:1 or from 1:2 to 2:1. Third column 126 is preferably a tray column as described above and preferably operates at atmospheric pressure. The temperature of the third distillate exiting from third column 126 preferably is from 60° C. to 110° C., e.g., from 70° C. to 100° C. or from 75° C. to 95° C. The temperature of the third residue in line 127 preferably is from 70° C. to 115° C., e.g., from 80° C. to 110° C. or from 85° C. to 105° C., when the column is operated at atmospheric pressure. Exemplary components of the distillate and residue compositions for third column 126 are provided in Table 6 below. It should be understood that the distillate and residue may also contain other components, not listed, such as components in the feed.

TABLE 6

ETHANOL PRODUCT COLUMN 126

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

As indicated above, when acid conversion is high in reactor 103, one column may be used to recover the ethanol product and water as the extractive agent. In FIG. 3 the first residue in line 116 is fed to a second column 129, referred to as the "water recovery column." The water from first residue in line 116 may be separated into the second residue in line 132 and returned to first column 107. There may be some acetic acid in second residue in line 132 and purge 133 may be taken as necessary.

In FIG. 3, the first residue in line 116 is introduced to the top part of second column 129, e.g., top half or top third. Although the temperature and pressure of second column 129 may vary, when at atmospheric pressure the temperature of the second residue exiting in line 132 preferably is from 70° C. to 120° C., e.g., from 90° C. to 115° C. or from 95° C. to 110° C. The temperature of the second distillate exiting in line 131 preferably is from 15° C. to 100° C., e.g., from 15° C. to 70° C. or from 40° C. to 70° C. The pressure of second column 129 may range from 0.1 kPa to 510 kPa, e.g., from 1 kPa to 475 kPa or from 1 kPa to 375 kPa. Exemplary components for the distillate and residue compositions for second column 129 are provided in Table 7 below.

TABLE 7

WATER RECOVERY COLUMN 129

|  | Conc. (wt. %) | Conc. (wt. %) | Conc. (wt. %) |
|---|---|---|---|
| Distillate |  |  |  |
| Ethanol | 70 to 96 | 80 to 93 | 85 to 93 |
| Water | 5 to 30 | 5 to 20 | 5 to 15 |
| Acetaldehyde | <30 | 0.01 to 10 | 0.01 to 5 |
| Ethyl Acetate | <1.5 | <1 | <0.01 |

TABLE 7-continued

WATER RECOVERY COLUMN 129

|  | Conc. (wt. %) | Conc. (wt. %) | Conc. (wt. %) |
|---|---|---|---|
| Residue |  |  |  |
| Water | 90 to 99 | 92 to 99 | 95 to 99 |
| Ethanol | <5 | 0.001 to 2 | 0.005 to 1 |
| Acetic Acid | 1 to 10 | 1 to 6 | 1 to 5 |

Returning to the first distillate in line 117, which comprises ethyl acetate and/or acetaldehyde, preferably is refluxed as shown in FIG. 1, for example, at a reflux ratio of from 1:30 to 30:1, e.g., from 1:5 to 5:1 or from 1:3 to 3:1. In one aspect, not shown, the first distillate or a portion thereof may be returned to reactor 103. In some embodiments, it may be advantageous to return a portion of first distillate to reactor 103. The ethyl acetate and/or acetaldehyde from the first distillate may be further reacted in hydrogenation reactor 103 or in a secondary reactor. The outflow from the secondary reactor may be fed to reactor 103 to produce additional ethanol or to a distillation column to recover additional ethanol.

In some embodiments, the first distillate in line 117 may also comprise minor amounts of water. If all or a portion of the first distillate is returned to the reactor, it may be necessary to remove water from line 117. The water from the first distillate in line 117 may be removed, for example, by an adsorption unit, one or more membranes, molecular sieves, extractive distillation, or a combination thereof. For example, an adsorption unit (not shown) may be used to remove a water stream from first distillate in line 117 thus producing a refined light stream preferably comprising less than 1 wt. % water and more preferably less than 0.5 wt. % water. Adsorption unit may remove up to 99.99% of the water from the first distillate in line 117, and more preferably from 95% to 99.99% of the water from the first distillate. Refined light stream, or a portion thereof, may be returned to reactor 103.

In one embodiment, the first distillate in line 117, or a portion of either or both streams, may be further separated to produce an acetaldehyde-containing stream and an ethyl acetate-containing stream. This may allow a portion of either the acetaldehyde-containing stream or ethyl acetate-containing stream to be recycled to reactor 103, while purging the other stream. The purge stream may be valuable as a source of either ethyl acetate and/or acetaldehyde.

The columns used in the present invention may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

Distillate in lines 119, 128, and 131 comprise ethanol, as discussed above, and may be further purified to form an anhydrous ethanol product stream, i.e., "finished anhydrous ethanol," using one or more additional separation systems, such as, for example, distillations (e.g., a finishing column), pressure swing absorption system, membrane, molecular sieves, extractive distillation, or a combination thereof.

Any of the compounds that are carried through the distillation process from the feed or crude reaction product generally remain in the ethanol distillate in amounts of less 0.1 wt. %, based on the total weight of the ethanol distillate composition, e.g., less than 0.05 wt. % or less than 0.02 wt. %. In one embodiment, one or more side streams may remove impurities from any of the columns in the system 100. Preferably at least one side stream is used to remove impurities from the third column. The impurities may be purged and/or retained within the system 100.

The final ethanol composition obtained by the process of the present invention may be taken from the third distillate or optionally from the second distillate. The ethanol product may be an industrial grade ethanol comprising 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 8.

TABLE 8

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt.

%, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be greater than indicated in Table 6, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882, 244 and zeolite Y in U.S. Pat. No. 3,130,007, the entireties of which are hereby incorporated herein by reference.

In order that the invention disclosed herein may be more efficiently understood, an example is provided below. It should be understood that this example is for illustrative purposes only and is not to be construed as limiting the invention in any manner.

EXAMPLE 1

The following examples were prepared with ASPEN Plus™ V7.1 simulation software to test various feed composition and separation systems.

A crude ethanol product comprising 56 wt. % ethanol, 38 wt. % water, 2% acetaldehyde, 2% ethyl acetate, 1 wt. % acetic acid, and 1 wt. % other organics is fed to column. This column contains 75 trays with the extractive agent feed location at the 1st tray from the top and crude ethanol product feed location at the 14th tray from the top. The flow rate of the crude ethanol product is 341502 lb/hr. The reflux rate is 11 times the distillate rate. The distillate temperature was about 65° C. and the residue temperature was about 103° C. to 107° C. The pressure of the column was 170.3 kPa. The distillate and residue compositions for three separate runs are shown in Table 9. Run A was without any extractive agent feed at a location above the crude ethanol product. Runs B and C used water as an extractive agent.

TABLE 9

|  | Run A | Run B | Run C |
|---|---|---|---|
| Extractive Agent flow rate (lb/hr) | 0 | 125,000 | 250,000 |
| Distillate (wt. %) |  |  |  |
| Ethanol | 25.0 | 0.6 | 1.9 |
| Water | 6.0 | 7.4 | 6.3 |
| Ethyl Acetate | 31.2 | 37.5 | 37.2 |
| Acetic Acid | <0.01 | <0.01 | <0.01 |
| Acetaldehyde | 27.3 | 27.3 | 27.3 |
| Other organics | 10.5 | 27.3 | 27.3 |
| Residue (wt. %) |  |  |  |
| Ethanol | 57.8 | 42.7 | 33.3 |
| Water | 39.9 | 56.6 | 66.1 |
| Ethyl Acetate | 0.4 | <0.01 | <0.01 |
| Acetic Acid | 1.0 | 0.7 | 0.6 |
| Acetaldehyde | <0.01 | <0.01 | <0.01 |
| Other organics | 1.0 | <0.01 | <0.01 |
| % of Ethanol Recovered in Residue | 97.5 | 99.9 | 99.8 |
| % of Ethyl Acetate Recovered in Distillate | 82.5 | 99.6 | 99.9 |
| Energy (MMBtu per ton of ethanol refined) | 0.73 | 0.80 | 1.02 |
| Ethyl Acetate Leakage in residue (wppm) | 3863 | 59 | 12 |

For Runs B and C, the presence of an extractive agent, allowed for decreased amounts of ethyl acetate leakage into the residue over Run A. In addition, higher ethanol recovery rates were demonstrated in Runs B and C based on the ASPEN simulation.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
    hydrogenating acetic acid from an acetic acid feed stream in a reactor to form a crude ethanol product comprising ethanol, ethyl acetate, water, and acetic acid;
    feeding an extractive agent comprising water and at least a portion of the crude ethanol product to a first column;
    separating at least a portion of the crude ethanol product in a first column into a first distillate comprising from 35 to 80 wt. % ethyl acetate, from 0.1 to 15 wt. % ethanol, from 2 to 25 wt. % water, from 0.1 to 30 wt. % acetaldehyde, and from 0.1 to 30 wt. % acetal, and a first residue comprising ethanol, acetic acid, and water, wherein the first residue comprises less than 1 wt. % ethyl acetate;

separating the first residue in a second column into a second distillate comprising ethanol, and a second residue comprising water and acetic acid; and recovering the extractive agent from the second residue.

2. The process of claim 1, wherein the first residue comprises less than 0.3 wt. % ethyl acetate.

3. The process of claim 1, wherein the recovered extractive agent is returned to the first column.

4. The process of claim 1, further comprising the steps of separating the second residue in a third column into a third distillate comprising water, and a third residue comprising acetic acid.

5. The process of claim 1, wherein the first residue comprises from 1 wppm to 800 wppm ethyl acetate.

6. The process of claim 1, wherein the first distillate comprises from 35 to 60 wt. % ethyl acetate, from 0.5 to 10 wt. % ethanol, from 4 to 15 wt. % water, from 5 to 30 wt. % acetaldehyde, and from 5 to 30 wt. % acetal.

7. The process of claim 1, wherein the first distillate comprises less than 0.2 wt. % acetic acid.

8. The process of claim 1, wherein the mass flow of water to crude ethanol product fed to the first column is from 2:1 to 1:15.

9. The process of claim 1, wherein the extractive agent is added above the portion of the crude ethanol product fed to the first column.

10. The process of claim 1, wherein the extractive agent is co-produced in the reactor.

11. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

12. A process for producing ethanol, comprising the steps of:

hydrogenating acetic acid from an acetic acid feed stream in a reactor to form a crude ethanol product comprising ethanol, ethyl acetate, water, and acetic acid;

feeding an extractive agent comprising water and at least a portion of the crude ethanol product to a first column;

separating at least a portion of the crude ethanol product in a first column into a first distillate comprising from 35 to 80 wt. % ethyl acetate, from 0.1 to 15 wt. % ethanol, from 2 to 25 wt. % water, from 0.1 to 30 wt. % acetaldehyde, and from 0.1 to 30 wt. % acetal, and a first residue comprising ethanol, acetic acid, and water, wherein the first residue comprises less than 1 wt. % ethyl acetate;

separating the first residue in a second column into a second distillate comprising ethanol and water, and a second residue comprising acetic acid;

separating the second distillate in a third column into a third distillate comprising ethanol, and a third residue comprising water; and recovering the extractive agent from the third residue.

13. The process of claim 12, wherein the first residue comprises less than 0.3 wt. % ethyl acetate.

14. The process of claim 12, wherein the recovered extractive agent is returned to the first column.

15. The process of claim 12, wherein the first residue comprises from 1 wppm to 800 wppm ethyl acetate.

16. The process of claim 12, wherein the first distillate comprises from 35 to 60 wt. % ethyl acetate, from 0.5 to 10 wt. % ethanol, from 4 to 15 wt. % water, from 5 to 30 wt. % acetaldehyde, and from 5 to 30 wt. % acetal.

17. The process of claim 12, wherein the first distillate comprises less than 0.2 wt. % acetic acid.

18. The process of claim 12, wherein the mass flow of water to crude ethanol product fed to the first column is from 2:1 to 1:15.

19. The process of claim 12, wherein the extractive agent is added above the portion of the crude ethanol product fed to the first column.

20. The process of claim 12, wherein the extractive agent is co-produced in the reactor.

21. The process of claim 12, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

* * * * *